United States Patent [19]
Fauconet et al.

[11] Patent Number: 5,510,514
[45] Date of Patent: Apr. 23, 1996

[54] PROCESS FOR THE PRODUCTION OF ALKYL (METH)ACRYLATES BY DIRECT ESTERIFICATION

[75] Inventors: Michel Fauconet, Valmont; Norbert Richard, Creutz Wald; Marc Esch, Frey Ming - Merlebach; Nadine Colin, Saint-Avold, all of France

[73] Assignee: Elf Atochem S.A., Puteaux, France

[21] Appl. No.: 187,282

[22] Filed: Jan. 27, 1994

[30] Foreign Application Priority Data

Jan. 27, 1993 [FR] France ................................. 93 00827

[51] Int. Cl.$^6$ ........................................... C07C 67/48
[52] U.S. Cl. ........................................... 560/218
[58] Field of Search ............................... 560/218

[56] References Cited

U.S. PATENT DOCUMENTS 4,968,834  11/1990  Smith et al. ............................ 560/218

FOREIGN PATENT DOCUMENTS 0463434  1/1992  European Pat. Off. .
4019781  1/1992  Germany .

OTHER PUBLICATIONS

*Patent Abstracts of Japan*, vol. 015, No. 163 (C–0826), Jan. 24, 1991 (Abstract of Japanese Publication No. 30 34 956).

*Primary Examiner*—Paul J. Killos
*Attorney, Agent, or Firm*—Millen, White, Zelano, & Branigan

[57] ABSTRACT

An alkyl (meth)acrylate is prepared by a direct esterification (in 1) of (meth)acrylic acid by the corresponding alcohol, catalysed by $H_2SO_4$. To the crude reaction mixture ($C_1$) comprising the desired ester, alcohol, (meth)acrylic acid, alkyl hydrogen sulphate and traces of $H_2SO_4$, there is added (in 3) a base to neutralize the acidic species, the resulting salts passing into the aqueous phase ($A_1$), which is separated from the organic phase ($O_1$) containing the desired ester. The light products ($L_1$) containing the alcohol are recovered (in 4) from the aqueous phase, and the waste waters ($W_2$) are expelled. A hydrolysis is carried out (in 8) of the alkyl hydrogen sulphate present in the aqueous phase ($A_1$) obtained after the separation which is carried out after neutralization (in 3), to form the alcohol and $H_2SO_4$ in this phase, the acidic species resulting from the hydrolysis are neutralized by introduction of a base .into the medium, and the resulting aqueous phase ($A_3$) is directed to the step for recovery of the alcohol. Pollution of the waters ($W_2$), attributable to the alkyl hydrogen sulphate, is thus avoided.

14 Claims, 4 Drawing Sheets

PROCESS FOR THE PRODUCTION OF ALKYL (METH)ACRYLATES BY DIRECT ESTERIFICATION

BACKGROUND OF THE INVENTION

The present invention relates to an improved process for the production of linear, branched or cyclic $C_1$–$C_{15}$ alkyl (meth)acrylates, by a direct esterification of (meth)acrylic acid with the corresponding alcohol, this reaction being catalysed by sulphuric acid.

The problems which arise regarding this production will now be explained, for convenience, on the basis of the example of the direct esterification of acrylic acid with butanol. These problems and the solution proposed by the invention are the same with regard to the use, on the one hand of methacrylic acid and, on the other hand of alcohols other than butanol.

Thus, the industrial process for the production of butyl acrylate involves a reaction of direct esterification of acrylic acid with butanol, which reaction is catalysed by sulphuric acid. In this process, the function of shifting the reaction equilibrium is provided for, not by the addition of a solvent which azeotropically entrains the water of reaction, but by an excess of the esterifying alcohol (in this case, butanol), which has the property of forming an azeotrope with water.

On conclusion of the reaction step which is carried out discontinuously, virtually all of the sulphuric acid has been converted to butyl hydrogen sulphate $BuSO_4H$, according to the following esterification reaction of sulphuric acid with butanol:

$$BuOH + H_2SO_4 \rightarrow HBuSO_4 + H_2O$$

Consequently, the reaction mixture at the end of the reaction contains butyl acrylate, butanol, acrylic acid, butyl hydrogen sulphate, traces of sulphuric acid, and the stabilizers conventionally used in the reaction.

The esterification reaction is followed by purification steps, which are generally carried out in continuous fashion:

the acidic species contained in the crude reaction mixture are neutralized, by addition thereto of an aqueous solution of base (sodium hydroxide); during this step, the acrylic acid is neutralized to give sodium acrylate, the butyl hydrogen sulphate to give neutral butyl sulphate $BuSO_4Na$, and the traces of sulphuric acid to give sodium sulphate $Na_2SO_4$, all these salts passing into the aqueous phase;

the separated organic phase, obtained after neutralization, is washed with water in an extraction column in order to remove the traces of impurities, of sodium hydroxide and of salts, and the washed butyl acrylate is then sent to a first distillation column, which allows the light products to be removed at the head, which products are recycled to the esterification reaction. The ester freed of this light fraction is then sent to a second column, from which it emerges at the head, purified by removal of the heavy products;

the butanol present is recovered:

in the separated aqueous phase obtained after neutralization, which essentially contains neutral butyl sulphate, butanol, sodium acrylate and traces of sodium sulphate;

in the aqueous phase obtained after the actual esterification reaction; and in the aqueous phase obtained after washing of the organic phase in the extraction column, this recovery of the butanol being carried out in a distillation column supplied at the head with the waters to be treated, in which the butanol is entrained at the head and can be recycled to the esterification reaction, while the foot of the column consists of the waste waters, which are freed of butanol and which will be passed to the biological treatment plant.

These waster waters thus expelled contain a large amount of organic pollution, measured by the chemical oxygen demand (COD) due to the presence of:

neutral butyl sulphate: the COD theoretically expelled is of the order of 2 kg of $O_2$ per kg of sulphuric acid involved in the esterification reaction;

sodium acrylate: the theoretical COD, due to the presence of residual acrylic acid at the end of the reaction, is approximately 8 kg of $O_2$ per tonne of butyl acrylate produced, which is approximately equivalent to a quarter of the COD due to the neutral butyl sulphate; it can be increased by a partial hydrolysis of the butyl acrylate in the course of the purification steps of the said ester.

The pollution due to butyl hydrogen sulphate (or the neutral butyl sulphate) could be avoided by using acid catalysts other than sulphuric acid which have the property of not giving an alcoholysis reaction with the alcohol. For example, it is known that methanesulphonic acid (MSA) and para-toluenesulphonic acid (PTSA) do not react, or react to only a small extent, with alcohols, to form alkyl sulphates. However, these catalysts have the disadvantage of being much more expensive than sulphuric acid, which makes it necessary to perform a recovery of these catalysts at the end of the reaction for the purpose of recycling them. This recovery, which could be envisaged by extraction with water, is not suitable here because of the presence of excess alcohol to remove the water of reaction, this alcohol playing the part of a competitive solvent with respect to the water, and thereby limiting the extraction yield of the catalyst into the water.

Other techniques may be envisaged for reducing the pollution due to the alkyl sulphate, but they all have disadvantages:

a hydrolysis of the alkyl hydrogen sulphate may be carried out in the organic reaction medium itself at the end of the esterification reaction, as is described in the article by J. WASILEWSKI, G. KESICKA, H. SMOLIK, E. CHROMIAK, Przemysl Chemiczny, 11–12 60, 1981, 541–543. In this article, the authors describe the hydrolysis of 2-ethylhexyl sulphate in the final reaction medium of synthesis of 2-ethylhexyl acrylate, at 80°–105° C., with 7.5% by weight of water, for 15 to 30 minutes. The main disadvantages are:

a low efficiency of removal of the 2-ethyl hexyl hydrogen sulphate;

hydrolysis of the 2-ethyl hexyl acrylate ester produced, which results in a loss of product and an increase in the pollution expelled in the form of acrylic acid (or sodium acrylate after neutralization);

the need to treat a sizeable flux, since it is all of the crude reaction mixture from the end of the esterification reaction which is treated;

a risk of damaging the quality and the stability of the 2-ethyl hexyl acrylate, which is a polymerizable ester.

it is also possible to envisage extraction of the butyl hydrogen sulphate with water, followed by a new extraction with the esterifying alcohol, as featured in German Patent Application DE-A-4,019,781. This approach to the describe problem is not applicable in the case of the process for the production of alkyl (meth)acrylates by direct esterification, because the excess alcohol (butanol) acts as a dissolving intermediary and greatly limits the extraction yield of the butyl hydrogen sulphate into the water. To be applicable, it would be necessary to employ a solvent, which would complicate the process, especially for the recovery and recycling of this solvent.

SUMMARY OF THE INVENTION

The inventors have therefore sought a new approach to the problem posed, and have discovered that the hydrolysis of the butyl (in general alkyl) hydrogen sulphate in the aqueous phase of the neutralization step (where it is present in its salt form) results in a substantial reduction in the pollution found in the spent waste water from a facility for the production of butyl acrylate: the COD is reduced by at least a factor of 5 (for example, as shown by a comparison between Reference Example 1 below and Example 2B of the invention). The cost of treatment at the purification plant is thus reduced. Furthermore, this hydrolysis makes it possible to recover and to recycle the butanol which has reacted with the sulphuric acid. This recovered butanol, which was otherwise lost, represents approximately 11 kg per tonne of butyl acrylate produced. It may be emphasized here that a saponification of $HBuSO_4$ in its salt form ($NaBuSO_4$) according to the reaction:

$$NaBuSO_4 + NaOH \rightleftharpoons Na_2SO_4 + BuOH$$

leads to very poor yields. Thus, the yields of a saponification (according to NaOH consumed) of a solution of $NaBuSO_4$ at a concentration of 5% by weight in water per 2 mol of NaOH/mole of $NaBuSO_4$ at 130° C., were 4.9%, 7% and 8.5% at the end of 1, 2 and 3 hours, respectively.

The principle of the treatment according to the invention, which is applicable to other alcohols and to methacrylic acid as has been mentioned above, therefore consists in hydrolysing butyl hydrogen sulphate, so as to regenerate butanol and sulphuric acid:

$$HBuSO_4 + H_2O \rightarrow BuOH + H_2SO_4$$

The regenerated butanol is easily eliminated in the aqueous phase obtained after this treatment, by distillation in the existing column. In this manner, all the pollution attributable to butyl hydrogen sulphate (more exactly to neutral butyl sulphate after neutralization) is eliminated.

The technique proposed according to the invention has the advantage, with respect to the technique which consists in hydrolysing the butyl hydrogen sulphate in the crude mixture obtained after esterification, in addition to an improved efficiency, of treating an aqueous phase having a very low concentration of hydrolysable and polymerizable final ester, and therefore of avoiding any risk of decreasing the production yield or of damaging the quality of the pure monomer. Furthermore, the volume employed in the hydrolysis reaction (minor aqueous flux with respect to the main organic flux containing the ester) is much smaller, and consequently requires a reactor of reduced size.

The subject of the present invention is therefore a process for the production of a $C_1$–$C_{15}$ alkyl (meth)acrylate by direct esterification of (meth)acrylic acid by the corresponding alcohol, the said esterification being catalysed by sulphuric acid, the crude reaction mixture obtained comprising $C_1$–$C_{15}$ alkyl (meth)acrylate, alcohol, (meth)acrylic acid, $C_1$–$C_{15}$ alkyl hydrogen sulphate, traces of sulphuric acid and the usual impurities, according to which process the esterification is followed by:

(a) addition to the said crude reaction mixture of a base to neutralize the (meth)acrylic acid, the $C_1$–$C_{15}$ alkyl hydrogen sulphate and the traces of sulphuric acid which are present therein, the resulting salts passing into the aqueous phase of the said mixture, the organic phase and the aqueous phase obtained from this neutralization being separated and the alkyl (meth)acrylate sought being recovered from the said organic phase;

(b) recovery of the alcohol from the said aqueous phase, the used waters, which are freed of the said alcohol, being expelled, characterized in that the alkyl hydrogen sulphate which is present in the aqueous phase obtained after the separation which is carried out after neutralization is hydrolysed so as to form the alcohol and sulphuric acid in the said phase, the acidic species resulting from the said hydrolysis are neutralized by introduction of a base into the medium, and the resulting aqueous phase is directed to the step for recovery of the alcohol.

This hydrolysis and the neutralization step which follows it may be carried out in continuous or discontinuous fashion.

In a particularly preferred embodiment, the hydrolysis is carried out in the presence of sulphuric acid as catalyst and agent for the neutralization of the basic species present, the said sulphuric acid being introduced in a molar ratio $R_H$, of the number of excess $H^+$ equivalents to the number of moles of alkyl hydrogen sulphate, which is at least equal to 1.5. For industrial implementation purposes, the molar ratio $R_H$ is preferably between 1.5 and 2.

Moreover, the hydrolysis is advantageously carried out at a temperature between approximately 70° and 200° C., for a time which depends upon the temperature applied, the pressure being dependent on the reaction temperature.

At the outlet of the hydrolysis reactor, the reaction medium is generally neutralized by addition of aqueous sodium hydroxide in the outlet pipe, and it is then cooled, generally to a temperature of the order of 60° C., for example through an exchanger This neutralization is intended to eliminate the excess sulphuric acid, to avoid corrosion of the apparatus downstream.

The step of recovery of the alcohol is carried out in a manner known per se, in a distillation column, the alcohol being entrained at the head in the said column.

The step of recovery of the (meth)acrylate ester is also carried out in a conventional manner, by washing with water, in an extraction column, the organic phase obtained after the phase separation which follows the first neutralization, then by directing the washed alkyl (meth)acrylate to a first distillation column, to remove at the head the light products, which are recycled to the esterification reaction, and, finally, by directing the alkyl (meth)acrylate which is freed of this light fraction to a second distillation column, from which it emerges at the head, purified by removal of the heavy products.

Finally, the abovementioned alcohol recovery column is supplied with:

the aqueous phase obtained after the actual esterification reaction;

the aqueous phase resulting from the hydrolysis after neutralization; and the aqueous phase obtained from the abovementioned extraction column.

As the alcohol, there may be mentioned methanol, butanol, hexanol, 2-ethylhexanol, and the like.

To illustrate better the subject of the present invention, several examples of are described below, with reference to the attached drawing, in which:

In the following, all the parts and all the percentages are expressed by weight, except where otherwise mentioned, BUHS and NBUS denoting butyl hydrogen sulphate and the neutral butyl sulphate, respectively, and EHHS and NEHS denoting 2-ethylhexyl hydrogen sulphate and neutral 2-ethylhexyl sulphate, respectively.

DETAILED DESCRIPTION OF THE DRAWINGS

Reference Example 1 (FIG. 1)—Production of butyl acrylate

Figure 1:
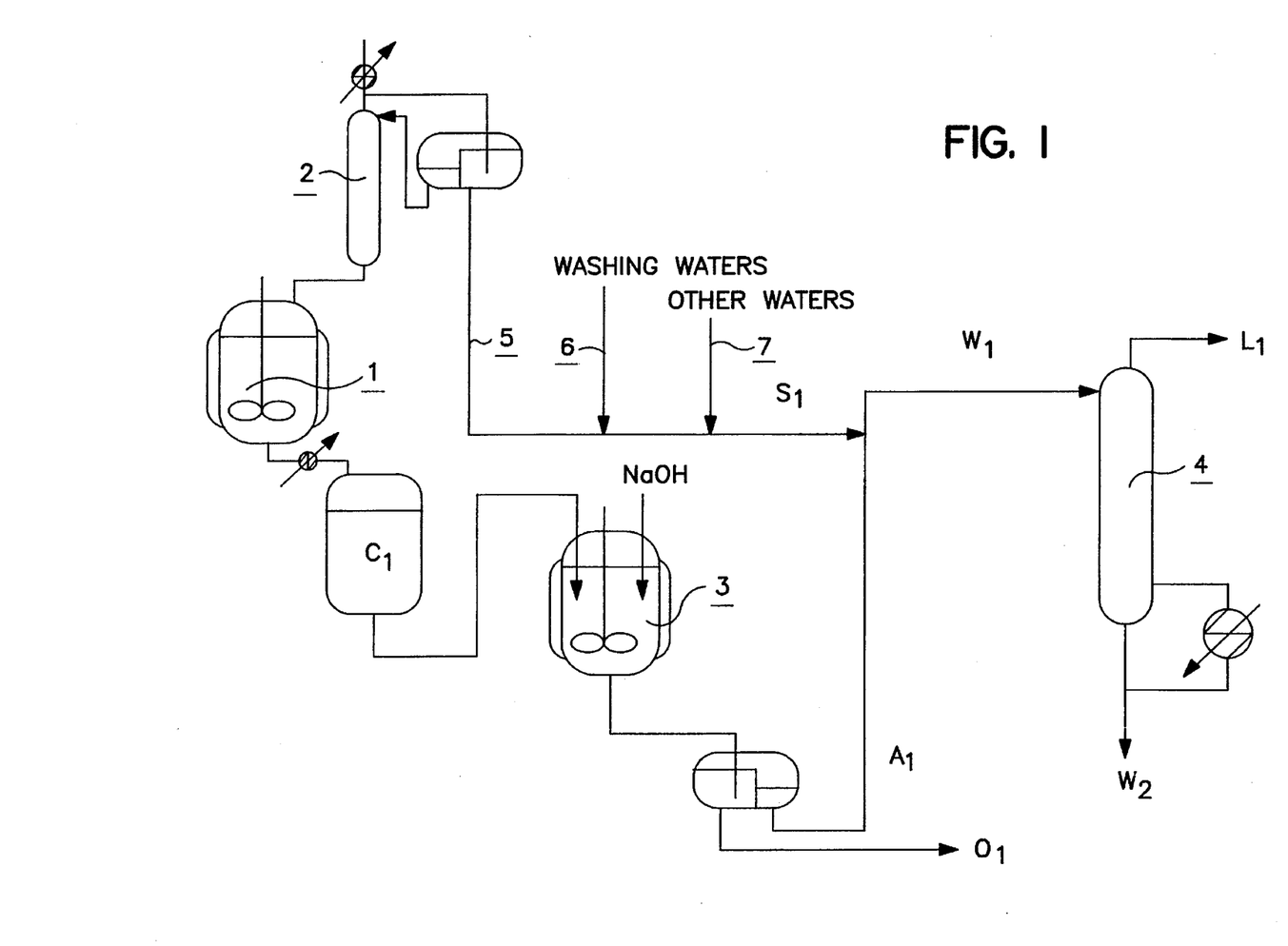
FIGS. 1 to 3 respectively show diagrams of the known process for the production of butyl acrylate or 2-ethylhexyl acrylate (cf. Reference Examples 1 and 5, respectively), of a process for the production of butyl acrylate or 2-ethylhexyl acrylate according to the invention (cf. Examples 2 and 6 of the invention, respectively) and of a process for the production of butyl acrylate with hydrolysis of butyl hydrogen sulphate in the crude reaction mixture (Comparative Example 3)

A—Synthesis of the crude reaction mixture:

An esterification of acrylic acid (1 part) with butanol (1.337 parts), in the presence of 94% sulphuric acid (0.025 part) as catalyst, and in the presence of polymerization inhibitors (0.002 part) is carried out discontinuously, in the stirred reactor 1, at a temperature of 80° C. at reduced pressure. The equilibrium of the esterification reaction is shifted towards formation of the expected butyl acrylate ester by distillation, in 2, of the water generated, in the form of an azeotropic mixture with butanol.

The composition of the post-reaction crude ($C_1$) is the following:

butyl acrylate: 79–81% butanol: 12–14% acrylic acid: 0.1–0.5% butyl hydrogen sulphate: 1.7–1.8% sulphuric acid: 0–0.02% water: 0.2–0.3%

B—Purification of the butyl acrylate (a) Neutralization of the acidic species

The reaction mixture ($C_1$) thus formed is neutralized to eliminate the acids present, namely butyl hydrogen sulphate, acrylic acid and traces of sulphuric acid. This neutralization takes place in the stirred reactor 3, discontinuously or continuously, using an 8% solution of sodium hydroxide, in slight excess (5%), over a period of 1 to 3 minutes, at a temperature of 20°–50° C. On conclusion of this neutralization, the mixture separates into two phases by settling: an organic phase ($O_1$) and an aqueous phase ($A_1$).

(b) Recovery of the alcohol

During production of the butyl acrylate, all the waste waters of the plant ($W_1$) are combined and sent to the head of a distillation column 4, which allows separation of the light compounds ($L_1$) (butanol and butyl acrylate, which are recovered at the head with a view to being recycled) from the spent waters ($W_2$), which are sent to the final station for biological treatment.

To simulate this part of the production of butyl acrylate, a distillation column was used which provides for a separation into a head fraction: 25–27% tail fraction: 73–75%.

This column is supplied at the head, continuously, with a mixture which is representative of the industrial mixture ($W_1$), which consists of:

the aqueous phase ($A_1$), obtained by neutralization of the crude mixture ($C_1$);

a synthetic mixture ($S_1$) representative of the other waste waters of the plant:

waters generated during the esterification reaction (symbolized by 5);

waters used for washing of the organic phase ($O_1$) (symbolized by 6);

other waters of the plant (symbolized by 7).

The composition of the mixture ($S_1$) is the following:

water: 96.3%;

butanol: 3%;

butyl acrylate: 0.3%;

other components: 0.4%.

The new mixture thus formed, which is representative of the industrial mixture ($W_1$), is composed of 1 part of ($A_1$) per 2.45 parts of ($S_1$).

C—Results

This reference test is carried out according to the procedure described above, without special treatment of the pollution expelled in the waste waters.

On conclusion of the reaction step, all of the sulphuric acid employed has been converted to butyl hydrogen sulphate in the mixture ($C_1$), and this compound passes entirely into the aqueous phase ($A_1$). After mixing of this aqueous phase with the synthetic mixture ($S_1$) in order to form the mixture ($W_1$), the spent waters ($W_2$) have a COD of 41.7 g of $O_2$ per kg of spent waters, of which 70 to 80% is due to the presence of butyl hydrogen sulphate.

Figure 2:
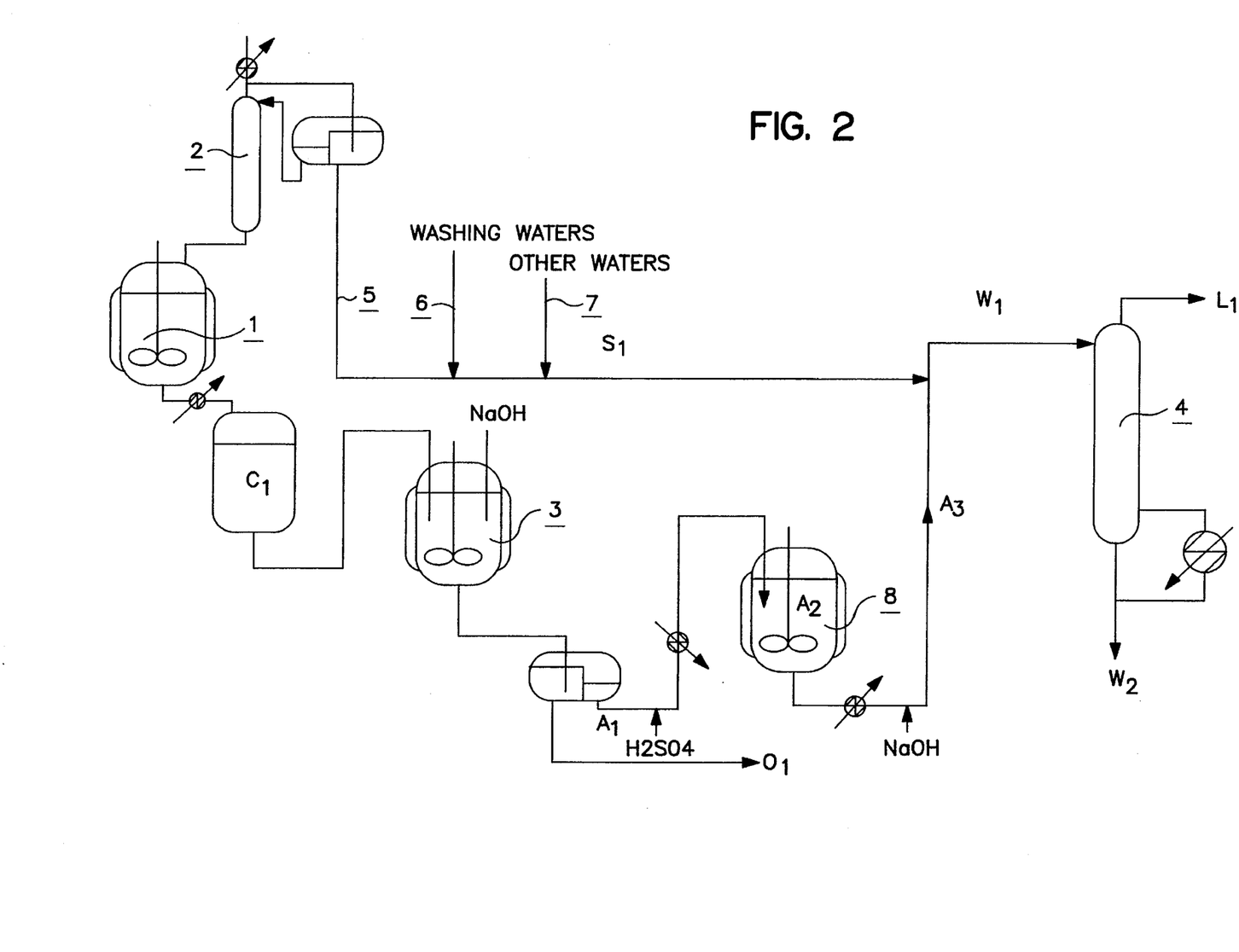

Example 2 of the invention FIG. 2)—Production of butyl acrylate

The process is performed as in Reference Example 1, but arrangement is made for elimination of the butyl hydrogen sulphate by acid hydrolysis of the neutral butyl sulphate contained in the aqueous phase ($A_1$). Experimentally, this reaction was carried out in two ways:

A—In discontinuous fashion:

The aqueous phase ($A_1$) mainly contains neutral butyl sulphate, sodium acrylate and excess sodium hydroxide. After determination of these three constituents, a quantity of 94% sulphuric acid is introduced such that, after neutralization of the excess sodium hydroxide and displacement of the acrylic acid from its sodium acrylate salt (NaA), the desired molar ratio obtained:

$R_H$=number of excess H⁺ equivalents/number of moles neutral butyl sulphate, which is equivalent to:

$R_H=(H^+)_{excess}/(NBUS)$ with: $(H^+)_{excess}=(H^+)_{introduced}-(NaA)-(NaOH)_{free}$.

In a reactor 8, equipped with a mechanical stirrer, the mixture, (A₂) thus formed is brought with stirring to a temperature T° for a time $t_R$.

At the end of this time, the mixture is cooled 70°–80° C., then neutralized with 8% NaOH to a pH of 8, to, eliminate the acidic species. A mixture (A₃) is thus, obtained, which is then introduced into the step for recovery of the alcohol in 4, in place of the mixture (A₁) of Reference Example 1.

Results

To verify under real conditions the results obtained on synthetic mixtures of butyl hydrogen sulphate (Example 4), a production of butyl acrylate was simulated, according to the conditions described Reference Example 1 (synthesis of the crude reaction mixture).

After the reaction step, the crude mixture obtained was neutralized discontinuously to eliminate the catalyst and the excess acrylic acid, which are again found, respectively, in the form of neutral butyl sulphate and sodium acrylate in the aqueous neutralization phase (A₁).

After addition of sulphuric acid to obtain a molar ratio $R_H=H^+/NBUS$ of 1.5, the new mixture (A₂) is introduced into the hydrolysis reactor 8 and brought to a temperature T° of 130° C., for a time $t_R$ of 1.5 hours. The mixture after reaction is neutralized to pH 8 using 8% NaOH. The phase (A₃) is then mixed with the synthetic mixture (S₁) to simulate the composition of the waste waters of the plant, and the mixture (W₁) thus formed is introduced continuously into the distillation column 4 for recovery of the butanol at the head and concentration of the spent waters which are intended for biological treatment at the foot.

The yield of hydrolysis of the neutral butyl sulphate is 97%, and the COD determined for the spent waters exiting at the foot of the column 4 is 6.1 g of O₂ per kg of water, which is equivalent to 15% of the COD obtained in the absence of treatment, of which virtually all is due to the presence of sodium acrylate.

B—In continuous fashion

The same hydrolysis reactor 8 as above is used, but the reaction mixture (A₂) is introduced continuously with the aid of a pump, and the temperature T° and residence time $t_R$ are varied. After a time equivalent to three times the complete renewal of the reactor, the hydrolysed mixture (A₃) is collected and then introduced into the distillation step 4 in place of the mixture (A₁).

Results

To simulate even more closely the operating conditions of the plant, the same type of simulation was performed as in the case of the discontinuous hydrolysis, but using steps of continuous neutralization of the crude mixture (C₁) after continuous reaction and hydrolysis of the aqueous neutralization phase (A₁).

The important parameters of the hydrolysis reaction were varied, within operating ranges close to those which had been determined by tests in tubes (Example 4), so as to define the optimum conditions thereof:

reaction temperature T° reaction time $t_R$.

The results of these tests performed in continuous fashion under different conditions are summarized in the following Table 1.

TABLE 1

| Hydrolysis of NBUS in an aqueous neutralization phase - tests performed in continuous fashion | | | | |
|---|---|---|---|---|
| Test No. | | 1 | 2 | 3 |
| H⁺/NBUS | mol | 1.5 | 1.5 | 1.5 |
| T° | °C. | 130 | 130 | 135 |
| Residence time | h | 1.5 | 2 | 2 |
| Hydrolysis yield | % | 84 | 97 | 96 |
| COD of spent waters | g/kg O₂ | | | 8 |

The hydrolysis yields are similar for residence times of 2 hours (95 to 97%). On the other hand, the results of test 1 show that a shorter residence time, for parameters which are otherwise equal (comparison of tests 1 and 2), leads to a lower efficiency.

The hydrolysis waters of test 3 are neutralized (mixture (A₃)) and then added to the synthetic mixture (S₁), and the mixture (W₁) thus formed is introduced continuously into the distillation column 4.

The COD measured for the spent waters recovered at the foot of the column is the following:

Test 3:

COD=8 g of O₂/kg of water, consequently 19% of the COD without hydrolysis.

Comparative Example 3 (FIG. 3)—Production of butyl acrylate

To compare the process according to the present invention with the process described by J. WASILEWSKI et al. in the abovementioned passage from the literature, which consists in hydrolysis of 2-ethylhexyl sulphate in the esterification reaction medium, a number of tests were carried out according to this method.

Figure 3:
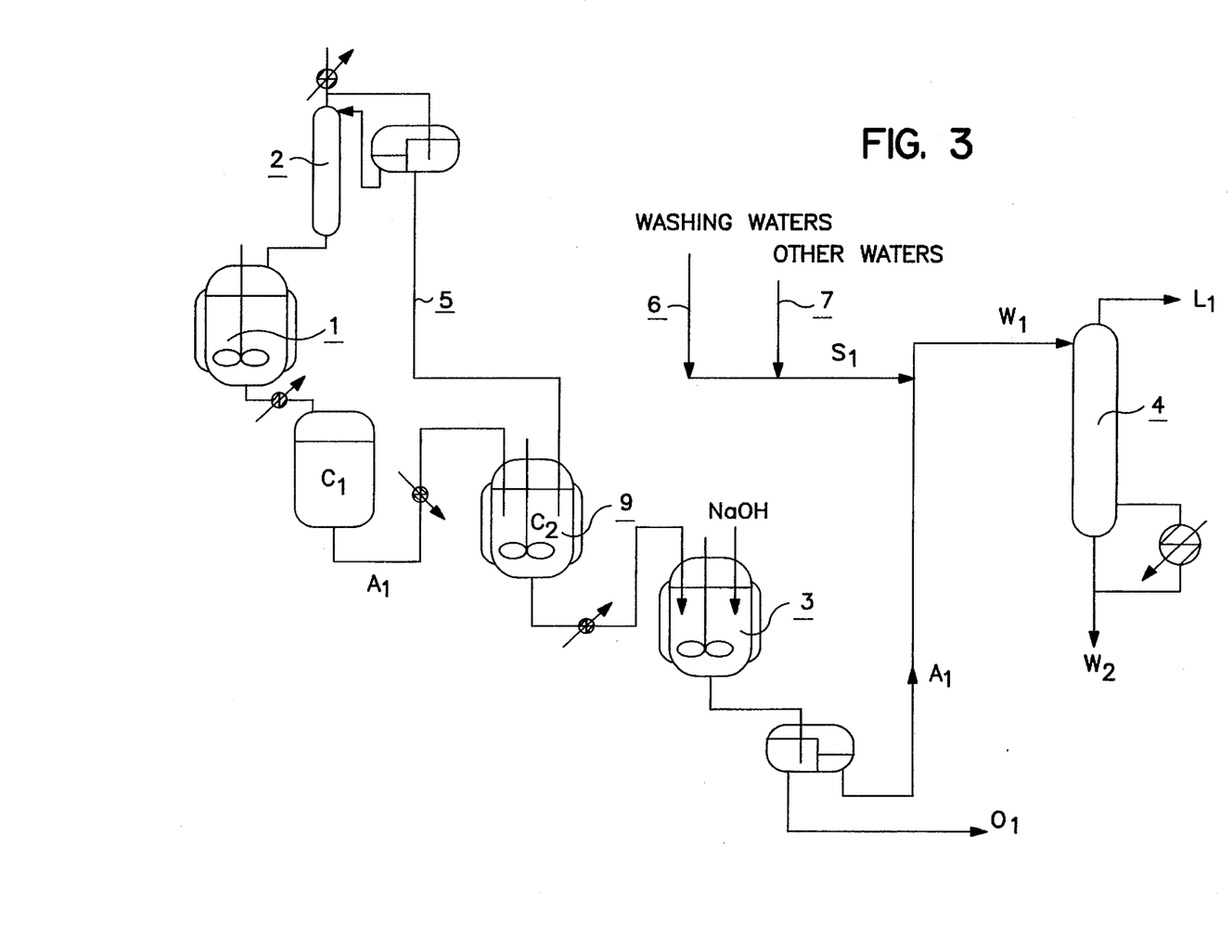

In a reactor 9, equipped with a mechanical stirrer, there are introduced the crude mixture (C₁) obtained after the main esterification reaction, together with the aqueous phase 5 collected in the azeotropic mixture distilled during the reaction (which represents 12% of the mixture thus formed). This mixture is brought to, and kept stirring at, a temperature T° for a time $t_R$. On conclusion of this step, the hydrolysed reaction mixture (C₂) follows the usual purification scheme described in Reference Example 1 (neutralization in place of the mixture (C₁), recovery of the alcohol).

Results

For the following operating conditions:

temperature=80° C.

duration=30 minutes water/crude=11.7%, the results for the complete simulation (hydrolysis of the butyl hydrogen sulphate in the crude mixture, neutralization, recovery of the alcohol) indicate that the treatment brings about a hydrolysis of 0.5% of the butyl acrylate produced by esterification.

The hydrolysis yield is only 65% with, as a consequence, a COD which is still relatively large in the spent waters: 21 g of O₂ per kg of water, which is equivalent to only 50% with respect to Reference Example 1, without hydrolysis, of which approximately 50% are due to butyl hydrogen sulphate, 35% to the acrylic acid which remains at the end of the esterification reaction and 15% to acrylic acid originating from hydrolysis of the butyl acrylate.

Example 4: Influence of the parameters of the acid hydrolysis of neutral butyl sulphate in the aqueous phase ($A_1$)

This study was performed in tubes, on a neutral synthetic solution of neutral butyl sulphate. This solution is prepared in the following manner:

In a stirred reactor, heated by an electric mantle and fitted with a condenser and equipment making it possible to work at reduced pressure, there are introduced 740 g of butanol (10 mol) and 202 g of 97% sulphuric acid (2 mol). The mixture is heated with stirring and refluxed for 3 hours at a temperature of 80° C. On conclusion of this reaction step, the mixture is cooled, then the acidity is neutralized with a solution of 2N sodium hydroxide to a pH=7–8. The excess butanol is distilled off and the neutral butyl sulphate obtained is diluted with water to a concentration of 5%.

This aqueous solution of neutral butyl sulphate is used to study the influence of the operating parameters on the hydrolysis reaction:

quantity of acids expressed as a molar ratio $R_H=H^+/NBUS$;

reaction temperature T°;

reaction time $t_R$.

The tests are performed in sealed tubes, immersed in a bath thermostated at the desired temperature.

Figure 4:
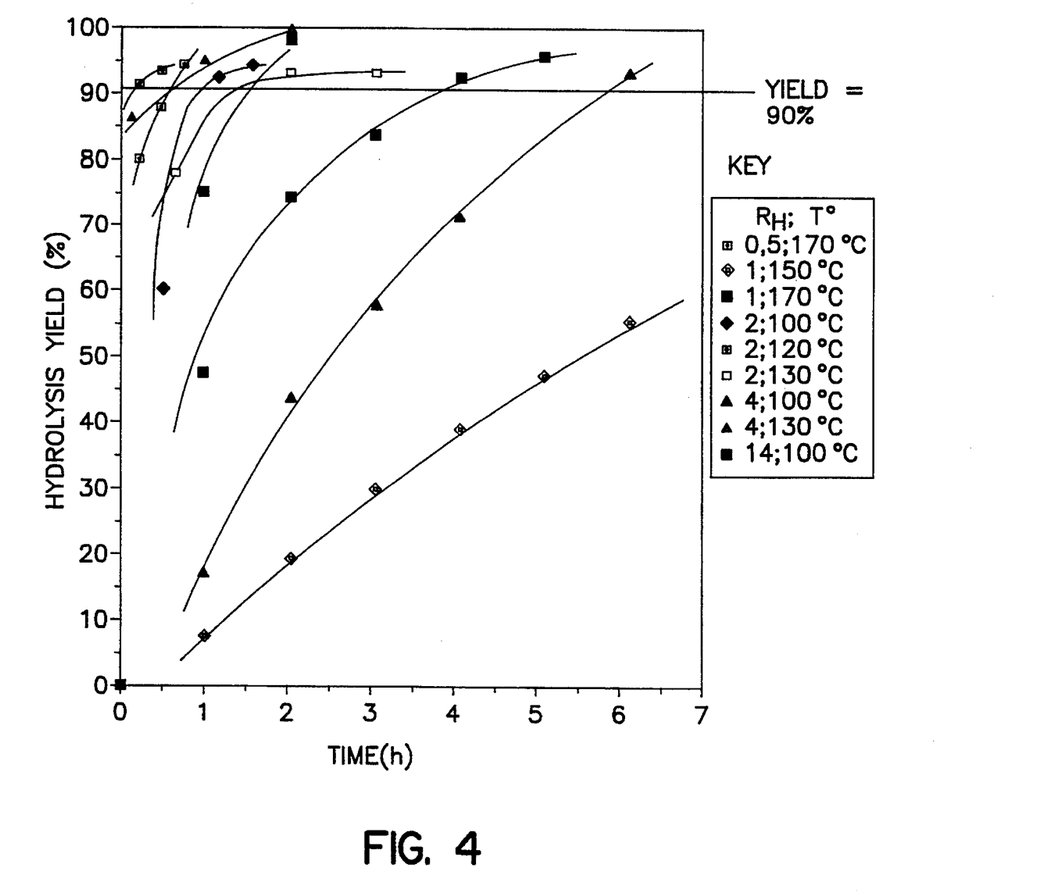
FIG. 4 illustrates the reaction kinetics for the hydrolysis of neutral butyl sulphate, giving different curves for the hydrolysis yield as a function of time, for various values of the hydrolysis temperature and of the $R_H$ ratio defined above.

The graph of FIG. 4 shows the yield of the hydrolysis of neutral butyl sulphate as a function of the hydrolysis time, for different quantities of sulphuric acid and different operating temperatures. From this graph, the time needed to hydrolyse 90% of the butyl sulphate present has been deduced. The values are reported in Table 2.

TABLE 2

| | Hydrolysis of NBUS in the synthetic aqueous phase - test in tubes | | | | | | | | | |
|---|---|---|---|---|---|---|---|---|---|---|
| $R_H = H^+/NBUS$ | | 0.5 | | 1 | | 2 | | | 4 | 14 |
| T° | °C. | 170 | 150 | 170 | 100 | 120 | 130 | 100 | 130 | 100 |
| $t_R$ | min | 30 | 55 | 5 | >420 | 205 | 75 | 330 | 185 | 85 |

Reference Example 5—Production of 2-ethylhexyl acrylate

A—Synthesis of the crude reaction mixture:

An esterification is carried out under the same conditions as in Reference Example 1 with the use of 2-ethylhexanol. The extent of conversion of $H_2SO_4$ into EHHS is 96%. The composition of the post-reaction crude ($C_1$) is as follows:

2-ethylhexyl acrylate: 70%

2-ethylhexanol: 25.7% acrylic acid 0.5%

2-ethylhexyl hydrogen sulphate (EHHS): 2.15% sulphuric acid: 0.04% water: 0.2%

B—Purification of 2-ethylhexyl acrylate (a) Neutralization of the acidic species:

In the same manner as for Reference Example 1 (paragraph B(a)), the acids present (EHHS, acrylic acid and sulphuric acid) are neutralized by NaOH in slight excess. On conclusion of this step, the mixture separates by settling to give an upper organic phase ($O_1$) and an aqueous phase ($A_1$).

(b) Recovery of the alcohol

In the same way as for the production of butyl acrylate, the distillation column 4 is supplied with a mixture ($W_1$) consisting of:

the abovementioned aqueous phase ($A_1$); and a mixture ($S_1$) which is representative of the other waste waters of the plant, of composition:

water: 98.9%

2-ethylhexanol: 0.30% other components: 0.8%

The new mixture ($W_1$) thus formed is composed of 1 part of ($A_1$) to 3 parts of ($S_1$).

C—Results

On conclusion of the reaction step, all of the sulphuric acid employed has been converted into EHHS in the mixture ($C_1$), and this compound passes entirely into the aqueous phase ($A_1$). After mixing of this aqueous phase with the synthetic mixture ($S_1$) to form the mixture ($W_1$), the spent waters ($W_2$) have a COD of 92.2 g of $O_2$ per kg of spent waters, of which 72% is due to the presence of EHHS, and the remainder to the presence of sodium acrylate and traces of undistilled 2-ethylhexyl acrylate.

Example 6 of the invention (FIG. 2)—Production of 2-ethylhexyl acrylate

The process is performed as in Example 2: after the synthesis step, the crude obtained is neutralized discontinuously to eliminate the catalyst and the excess acrylic acid, which are found respectively in the form of NEHS and sodium acrylate in the aqueous neutralization phase ($A_1$).

After addition of sulphuric acid to obtain a molar ratio $R_H=H^+/NEHS$ of 1.5, the new mixture ($A_2$) is introduced into the hydrolysis reactor and brought to a temperature T° of 130° C. for a time $t_R$ of 1.5 hours. The mixture after reaction is neutralized to pH 8 with 8% NaOH. The phase ($A_1$) is then mixed with ($S_1$) (1 part of ($A_3$) to 3 parts of ($S_1$)) to simulate the composition of the waste waters of the plant, and the mixture ($W_1$) thus formed is introduced continuously into the distillation column 4 for recovery of the 2-ethylhexanol at the head and concentration of the spent waters which are intended for biological treatment at the foot.

The yield of the hydrolysis of NEHS is 87 to 100%, and the COD determined for the spent waters exiting at the foot of column 4 is 20.7 g of $O_2$ per kg of spent waters, virtually all of which is due to the presence of sodium acrylate and undistilled residual alcohol.

We claim:

1. A process for the production of a $C_1$–$C_{15}$alkyl (meth)acrylate comprising:

(a) conducting a direct esterification of (meth)acrylic acid by a $C_1$–$C_{15}$ alcohol, said esterification being catalyzed by sulphuric acid and resulting in a crude reaction mixture comprising $C_1$–$C_{15}$ alkyl (meth)acrylate, the alcohol, (meth)acrylic acid, $C_1$–$C_{15}$ alkyl hydrogen sulphate, and sulphuric acid;

(b) adding to said crude reaction mixture an aqueous solution of a base to neutralize the (meth)acrylic acid, the $C_1$–$C_{15}$ alkyl hydrogen sulphate, and the sulphuric acid thereby forming an organic phase and an aqueous phase, the resulting salts passing into the aqueous phase of the said mixture;

(c) separating the resulting organic phase from the resultant aqueous phase;

(d) recovering the alkyl (meth)acrylate product from said organic phase;

(e) adding acid to said resultant aqueous phase and subjecting the alkyl hydrogen sulphate present in its salt form in said aqueous phase to acid hydrolysis so as to form a $C_1$–$C_{15}$ alcohol and sulphuric acid in the said phase;

(f) neutralizing the acidic species resulting from the said hydrolysis by introduction of a base into the medium; and (g) recovering the $C_1$–$C_{15}$ alcohol from the resulting aqueous phase from step (f).

2. A process for the production of a $C_1$–$C_{15}$ alkyl (meth)acrylate comprising:

(a) conducting a direct esterification of (meth)acrylic acid by a $C_1$–$C_{15}$ alcohol, said esterification being catalyzed by sulphuric acid and resulting in a crude reaction mixture comprising $C_1$–$C_{15}$ alkyl (meth)acrylate, the alcohol, (meth)acrylic acid, $C_1$–$C_{15}$ alkyl hydrogen sulphate, and sulphuric acid;

(b) adding to said crude reaction mixture an aqueous solution of a base to neutralize the (meth)acrylic acid, the $C_1$–$C_{15}$ alkyl hydrogen sulphate, and the sulphuric acid thereby forming an organic phase and an aqueous phase, the resulting salts passing into the aqueous phase of the said mixture;

(c) separating the resulting organic phase from the resultant aqueous phase;

(d) recovering the alkyl (meth)acrylate product from said organic phase, and organic phase; and (e) adding acid to said resultant aqueous phase and subjecting the alkyl hydrogen sulphate present in its salt form in said aqueous phase to acid hydrolysis so as to form a $C_1$–$C_{15}$ alcohol and sulphuric acid in the said phase.

3. A process according to claim 1, wherein the hydrolysis is carried out in continuous fashion.

4. A process according to claim 1, wherein the hydrolysis is carried out in discontinuous fashion.

5. A process according to claim 1, wherein that the hydrolysis is carried out in the presence of sulphuric acid as catalyst and agent for the neutralization of the basic species present, the said sulphuric acid being introduced in a molar ratio $R_H$, of the number of excess $H^+$ equivalents to the number of moles of alkyl hydrogen sulphate, which is at least equal to 1.5.

6. A process according to claim 1, wherein the hydrolysis is carried out at a temperature between 70° and 200° C.

7. A process according to claim 1, wherein the step of recovery of the alcohol is carried out in a first distillation column (4), the alcohol being entrained at the head in the said column (4).

8. A process according to claim 1, wherein the step of recovery of the ester is carried out by washing with water, in an extraction column, the organic phase ($O_1$) obtained after the phase separation which follows the first neutralization, then by directing the washed alkyl (meth)acrylate to a first distillation column, to remove at the head the light products, which are recycled to the esterification reaction, and, finally, by directing the alkyl (meth)acrylate which is freed of this light fraction to a second distillation column, from which it emerges at the head, purified by removal of the heavy products.

9. A process according to claim 8, wherein the first distillation column (4) is supplied with:

an aqueous phase (5) obtained after the esterification reaction, an aqueous phase ($A_3$) resulting from the hydrolysis after neutralization, and an aqueous phase (6) obtained from said extraction column.

10. A process according to claim 1, wherein the alcohol used is methanol, butanol, hexanol or 2-ethylhexanol.

11. A process according to claim 5, wherein the molar ratio $R_H$ is between 1.5 and 2.

12. A process according to claim 2, wherein the hydrolysis is carried out in the presence of sulphuric acid as catalyst and agent for the neutralization of the basic species present, the said sulphuric acid being introduced in a molar ratio $R_H$, of the number of excess $H^+$ equivalents to the number of moles of alkyl hydrogen sulphate, which is at least equal to 1.5.

13. A process according to claim 12, wherein the molar ratio $R_H$ is between 1.5 and 2.

14. A process according to claim 2, wherein the hydrolysis is carried out at a temperature between 70° and 200° C.

* * * * *